US008721935B2

(12) United States Patent
Grebennikov

(10) Patent No.: US 8,721,935 B2
(45) Date of Patent: May 13, 2014

(54) METHOD FOR PRODUCING LIPOSOMAL DRUGS AND A DEVICE FOR PRODUCING A LIPOSOME

(76) Inventor: Evgeny P. Grebennikov, Moscow (RU)

( * ) Notice: Subject to any disclaimer, the term of this patent is extended or adjusted under 35 U.S.C. 154(b) by 0 days.

(21) Appl. No.: 13/170,720

(22) Filed: Jun. 28, 2011

(65) Prior Publication Data

US 2011/0260347 A1 Oct. 27, 2011

Related U.S. Application Data

(63) Continuation of application No. PCT/RU2009/000172, filed on Apr. 9, 2009.

(30) Foreign Application Priority Data

Dec. 29, 2008 (RU) ................................ 2008151923

(51) Int. Cl.
*B01J 13/04* (2006.01)
*A61K 9/127* (2006.01)

(52) U.S. Cl.
USPC ................................ 264/4.1; 425/5; 424/450

(58) Field of Classification Search
USPC .............. 264/4, 4.1, 4.3, 4.32, 4.33; 428/402, 428/402.2; 427/212, 213, 213.3, 213.31, 427/213.33, 483
See application file for complete search history.

(56) References Cited

U.S. PATENT DOCUMENTS

2002/0001613 A1* 1/2002 Niemiec et al. ............... 424/450
2005/0032240 A1* 2/2005 Lee et al. ...................... 436/180
2005/0175683 A1 8/2005 Zhang

FOREIGN PATENT DOCUMENTS

GB 2145107 A 3/1985

OTHER PUBLICATIONS

International Search Report, mailed Sep. 3, 2009, from PCT/RU2009/000172, filed on Apr. 9, 2009.
International Preliminary Report on Patentability, mailed Jun. 29, 2011, from PCT/RU2009/000172, filed on Apr. 9, 2009.
Kovalnogov N.N.: "Rasschet techenia i soprotivlenia trenia potoka o soplakh Lavalia. Posobie k kursovoi rabote po gidrogazodinamike", 2001, pp. 11-21, Ul'ianovsk.

* cited by examiner

*Primary Examiner* — James J Seidleck
*Assistant Examiner* — S. Camilla Pourbohloul
(74) *Attorney, Agent, or Firm* — Patentbar International, P.C.

(57) ABSTRACT

The essence of the invention is that an aqueous medium is mixed with a lipid component (lipid solution in an organic solvent) by the ejecting introduction (suction) of the lipid component (lipid solution in an organic solvent) into an ejector mixing chamber in the form of a de Laval nozzle by means of the energy from a pressurized jet of the aqueous medium flowing out of the inlet nozzle of the ejector, which jet creates a pressure drop in the convergent part (confuser) of the mixing chamber, wherein an aerosol stream of liposome is formed at the outlet of the divergent part (diffuser) of the mixing chamber.

2 Claims, 1 Drawing Sheet

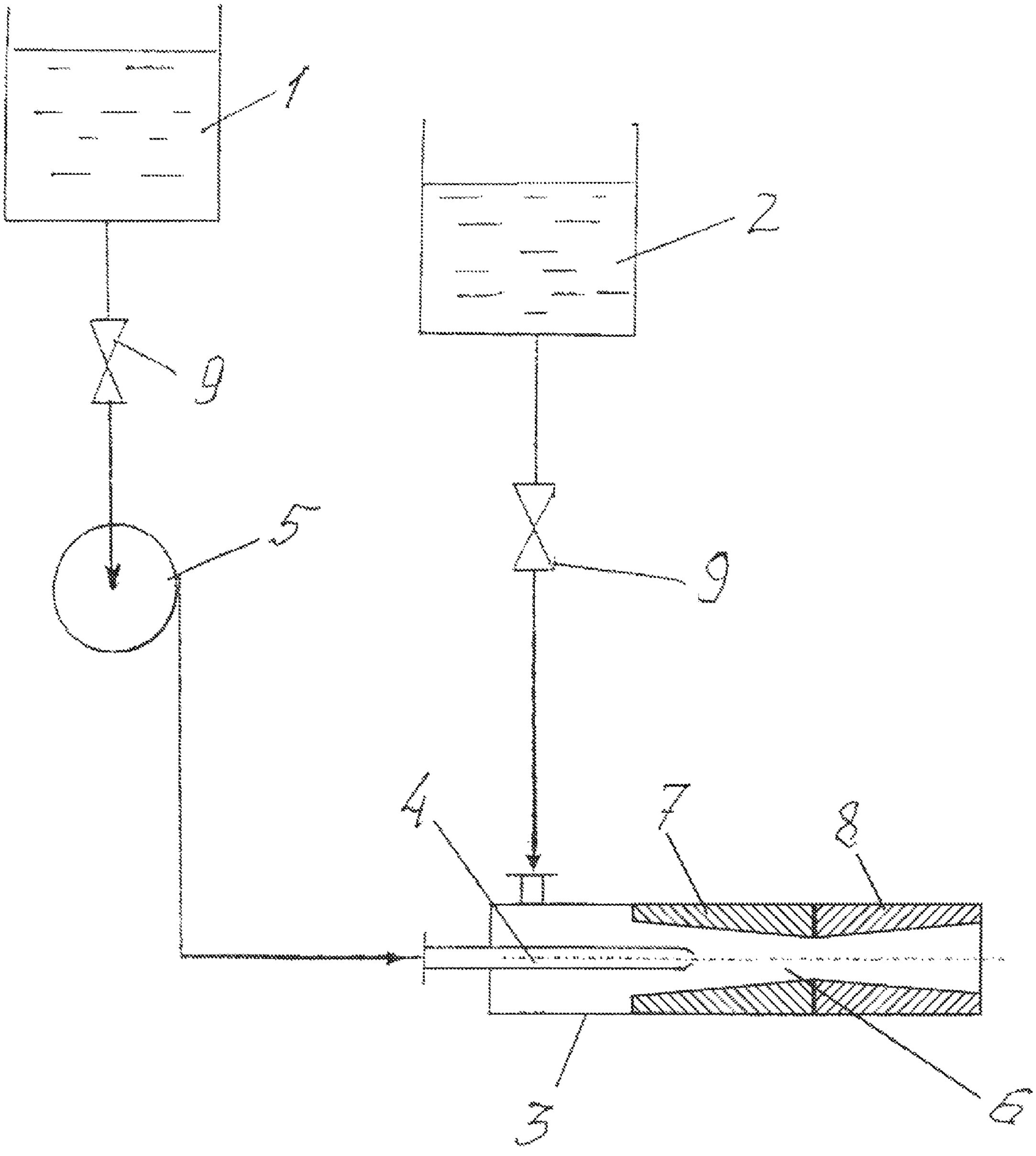
1
2
9
9
5
4
7
8
3
6

METHOD FOR PRODUCING LIPOSOMAL DRUGS AND A DEVICE FOR PRODUCING A LIPOSOME

RELATED APPLICATIONS

This Application is a Continuation application of International Application PCT/RU2009/000172 filed on Apr. 9, 2009, which in turn claims priority to Russian Patent Application No. 2008151923, filed Dec. 29, 2008, both of which are incorporated herein by reference in their entirety.

FIELD OF THE INVENTION

The invention relates to the field of applied biotechnology and may be used in medicine, cosmetology, veterinary medicine, crop science, etc., to increase the efficiency of the preparation of liposomal drugs in the form of an aerosol stream.

BACKGROUND OF THE INVENTION

A method is known from prior art for producing liposomal drugs in the form of an aerosol stream, including mixings of an aqueous medium, fed into a mixing chamber, with a lipid component—a solution of lipids in an organic solvent, and the subsequent formation of an aerosol stream by spraying from a nozzle with application to a surface to be treated (GB 2145107 A, 1985). However, the process of the preparation of liposomal vesicles by simple mixing of the lipid component—a solution of lipids, with an aqueous medium is insufficiently efficient.

A device is also known for producing liposomes in the form of an aerosol stream, including vessels with an aqueous medium and a lipid component—a solution of lipids in a water-soluble organic solvent, that are connected to a mixer with a spray nozzle at the outlet. (GB 2145107 A, A61J3100, 1985). In that device both components are fed into the mixer from the respective vessels under pressure created in the vessels by a propellant (a neutral gas); this complicates the device and does not ensure effective mixing of the components and a high degree of spraying—dispersion of the mixture formed.

SUMMARY OF THE INVENTION

The invention is directed toward increasing the efficiency of the production of liposomal drugs in the form of an aerosol stream and the creation of a simple and efficient device for producing liposomes.

The solution of the stated problem is achieved by the fact that, according to the invention, in the method for producing liposomes, that includes mixings of an aqueous medium, fed under pressure into a mixing chamber, with a lipid component—a solution of lipids in an organic solvent, and the subsequent formation of an aerosol stream by spraying from a nozzle with application to a surface to be treated, the mixing is accomplished by an ejector by means of the ejecting introduction—suction of the lipid component, of a solution of lipids in an organic solvent into the mixing chamber of the ejector made in the form of a Laval nozzle, by means of the energy of the jet of aqueous medium flowing out of the inlet nozzle of the ejector, which creates rarefaction in the narrowing part—the convergent tube, of the mixing chamber, with simultaneous dispersion and homogenization in the expanding part—the divergent tube, of the mixing chamber, wherein an aerosol stream of liposomes is formed at the outlet upon spraying from the expanding part of the divergent tube of the mixing chamber.

At the same time, the aqueous medium and/or the lipid component—a solution of lipids in an organic solvent, contain a biologically active substance.

In addition, the solution of the stated problem is also achieved by the fact that in the device for producing liposomes, that includes a vessel with an aqueous medium and a vessel with a lipid component—a solution of lipids in a water-soluble organic solvent, that are connected to a mixer with a spray nozzle at the outlet, according to the invention, a pump is included between the vessel with the aqueous medium and the mixer, wherein the mixer is made in the form of an ejector, the central inlet active flow nozzle of which is connected with the outlet pipe of the pump, and the mixing chamber is made in the form of a Laval nozzle, to the convergent tube of which is connected the vessel with the lipid component, and the divergent tube of which is a spray nozzle.

The construction of the mixer in the form of an ejector with a mixing chamber made in the form of a Laval nozzle with narrowing and expanding parts, provides, with simplicity of design, ejection (suction) of the lipid component into the mixing chamber by means of the energy of the jet of aqueous medium flowing out of the central inlet nozzle of the ejector that creates rarefaction in the narrowing part (convergent tube), while, due to the hydrodynamic action, intense dispersion and homogenization of the mixture of components flowing through at high velocity takes place in the expanding part (divergent tube), and upon outflow from the divergent tube, as from a spray nozzle, the efficient formation takes place of a flow of finely dispersed drops containing a solution of a biologically active substance with a lipid envelope, forming a stable bilayer membrane—a vesicle (liposome).

BRIEF DESCRIPTION OF THE DRAWINGS

In FIG. 1, the device for producing liposomal drugs is represented schematically.

DETAILED DESCRIPTION OF THE PREFERRED EMBODIMENTS

The device for producing liposomal drugs contains a vessel 1, filled with aqueous medium that can contain a biologically active substance; a vessel 2, with a lipid component-a solution of lipids in a water-soluble organic solvent, that also can contain a biologically active substance; a mixer, which is an ejector 3; a central active flow nozzle 4, is connected with the outlet pipe of a pump 5 included between vessel 1 and ejector 3. Mixing chamber 6 of ejector 3 is made in the form of a Laval nozzle, the convergent tube 7 of which is connected with the vessel 2 with the lipid component, and the divergent tube 8 of the Laval nozzle of mixing chamber 6 is a spray nozzle. Control valves 9 are mounted in the main pipelines connecting vessels 1 and 2 with ejector 3.

The method applied for, of producing liposomal drugs in the form of an aerosol stream, is implemented in the following manner.

The lipid component is a solution of phospholipids (individual phospholipids or a mixture of them, produced from plant, animal, or biotechnological raw material) in an organic water-soluble solvent (ethanol, propanol, benzyl alcohol, hexane, methanol, chloroform, ether, etc.), with a concentration no less than 0.5%, that can contain a biologically active substance, is poured into vessel 2, and vessel 1 is filled with an aqueous medium, for example, an aqueous solution of a biologically active substance. When the aqueous medium is delivered from vessel 1 into the central nozzle 4 of ejector 3 by pump 5 (or, as a variant, under pressure of a neutral gas—a propellant pumped into vessel 1), the jet of out-flowing active flow creates rarefaction in the convergent tube 7 of the Laval nozzle—mixing chamber 6 of ejector 3, due to which ejection (suction) of the lipid component—the phospholipid solution from vessel 2, takes place. In the divergent tube 8, the lipid component—the phospholipid solution, is actively mixed with the flow of the aqueous medium with the formation of a disperse homogeneous mixture of components, upon the spraying of which an aerosol stream of liposomes—finely dispersed drops containing a solution of a biologically active substance, with a lipid envelope forming a stable bilayer membrane—a vesicle (liposome), is formed at the outlet of the divergent tube 8 of the Laval nozzle—mixing chamber 6, as from a spray nozzle. The ratio of the flow rates of the components is controlled by means of valves 9. The aerosol stream formed, of the aqueous suspension of liposomes containing the biologically active substance, is delivered from the divergent tube 8 directly onto the surface to be treated, for example, the skin.

Example 1

To prepare the lipid component, a phospholipid extract (for example, Lipofolk) is dissolved in an organic water-soluble solvent (for example, ethanol—70% ethyl alcohol) until a 10% concentration of phospholipids is obtained and is mixed in a 1:1 ratio with a biologically active substance:an alcohol (in 70% ethyl alcohol) tincture of calendula—a preparation with antiseptic and anti-inflammatory properties, prepared from dry flowers in a 1:10 ratio. The lipid component obtained is poured into vessel 2, and vessel 1 is filled with distilled water. The aerosol stream of the aqueous suspension of liposomes that contain the biologically active substance—calendula (8-10% extract of calendula), that is formed as a result of the ejection mixing, is directed from the divergent tube 8 of the Laval nozzle—mixing chamber 6, as from a spray nozzle, onto the surface to be treated, for example, the skin.

Example 2

A lipid solution is prepared by dissolving a phospholipid extract (for example, Lipofolk) in an organic water-soluble solvent (for example, ethanol—70% ethyl alcohol) until a 10% concentration of phospholipids is obtained and is poured into vessel 2. Vessel 1 is filled with an aqueous medium (an aqueous solution of a biologically active substance), for example, an aqueous-alcoholic tincture of mountain arnica flowers in a 40% alcohol solution (extraction modulus 1:15). The aerosol stream that is formed as a result of the ejection mixing, of the aqueous suspension of liposomes, and that contains the biologically active substance—extract of mountain arnica, which improves local microcirculation and blood supply, promotes lymph drainage, maintains the tonus of veins, and removes edema of the legs, is directed from the divergent tube 8 of the Laval nozzle—mixing chamber 6, as from a spray nozzle, onto the surface to be treated, for example, the skin.

Example 3

To prepare the lipid component, a phospholipid extract (for example, Lipofolk) is dissolved in an organic water-soluble solvent (for example, ethanol—70% ethyl alcohol) until a 10% concentration of phospholipids is obtained and is mixed in a 1:1 ratio with a biologically active substance:a mixture of an alcoholic extract of arnica (an aqueous-alcoholic tincture of mountain arnica flowers in a 40% alcohol solution) and of camomile (an aqueous-alcoholic tincture of wild camomile flowers in a 40% alcohol solution) in a 1:1 ratio with the phospholipids (1:2). The lipid component obtained is poured into vessel 2. Vessel 1 is filled with an aqueous medium (an aqueous solution of a biologically active substance), containing a mixture in a 1:1 ratio of an aqueous extract of flowers of wild camomile 1:20 in a water bath and an aqueous extract of flowers of mountain arnica 1:20 in a water bath. The aerosol stream that is formed as a result of the ejection mixing, of the aqueous suspension of liposomes, and that contains the mixture of biologically active substances—camomile and arnica, which exerts a stimulating action on the processes of skin regeneration, is directed from the divergent tube 8 of the Laval nozzle—mixing chamber 6, as from a spray nozzle, onto the skin surface to be treated.

What is claimed is:

1. A method for producing liposomal drugs in an aerosol stream, comprising:

mixing of an aqueous medium, fed under pressure into a mixing chamber, with a lipid component, the lipid component being a solution of lipids in an organic solvent; and subsequently forming of an aerosol stream by spraying from a nozzle for applying to a surface to be treated, wherein the aerosol stream of liposomes is formed at an outlet upon spraying from an expanding part of the mixing chamber, the expanding part being a divergent tube; and wherein the mixing is accomplished in an ejector by suction-induced introduction of the lipid component into the mixing chamber of the ejector by means of jet energy of the aqueous medium flowing out of an inlet nozzle of the ejector, the aqueous medium flowing out creating rarefaction in a converging part of the mixing chamber, the converging part being a convergent tube, with simultaneous dispersing and homogenizing in the expanding part of the mixing chamber, the mixing chamber made in the form of a Laval nozzle.

2. The method for producing liposomal drugs in an aerosol stream according to claim 1, characterized by the aqueous medium and/or the lipid component comprising a biologically active substance.

* * * * *